(12) United States Patent
Seleem et al.

(10) Patent No.: US 11,806,342 B2
(45) Date of Patent: Nov. 7, 2023

(54) DIIODOHYDROXYQUINOLINE FOR THE TREATMENT OF CLOSTRIDIUM DIFFICILE INFECTION

(71) Applicant: Purdue Research Foundation, West Lafayette, IN (US)

(72) Inventors: Mohamed Seleem, West Lafayette, IN (US); Nader Abutaleb, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/063,750

(22) Filed: Oct. 6, 2020

(65) Prior Publication Data
US 2021/0100787 A1    Apr. 8, 2021

Related U.S. Application Data

(60) Provisional application No. 62/911,594, filed on Oct. 7, 2019.

(51) Int. Cl.
| | | |
|---|---|---|
| *A61K 38/14* | (2006.01) | |
| *A61K 9/00* | (2006.01) | |
| *A61K 31/47* | (2006.01) | |
| *A61K 31/7048* | (2006.01) | |
| *A61K 31/4164* | (2006.01) | |

(52) U.S. Cl.
CPC ............ *A61K 31/47* (2013.01); *A61K 9/0014* (2013.01); *A61K 9/0053* (2013.01); *A61K 31/4164* (2013.01); *A61K 31/7048* (2013.01); *A61K 38/14* (2013.01)

(58) Field of Classification Search
CPC ................ A61K 31/4164; A61K 31/47; A61K 31/7048; A61K 38/14; A61K 9/0014; A61K 9/0053; A61K 9/00
See application file for complete search history.

(56) References Cited

U.S. PATENT DOCUMENTS

2004/0077601 A1 *   4/2004   Adams ..................... A61P 35/02
                                                           514/64
2017/0354697 A1 * 12/2017   Schneider ................. A23L 5/00

FOREIGN PATENT DOCUMENTS

WO    WO-2009140215 A2 * 11/2009   ............. A61K 31/47

OTHER PUBLICATIONS

Lodoquinol from PubChem, https://pubchem.ncbi.nlm.nih.gov/compound/lodoquinol, pp. 1-8, enclosed. Accessed Mar. 8, 2022. (Year: 2022).*

Vindigni, S., et al., "C. difficile Infection: Changing Epidemiology and Management Paradigms", Clin Transl Gastroenterol, e99, pp. 6, 2015.
Lessa, F., et al., "Burden of Clostridium difficile Infection in the United States", N Engl J Med, 372(9), pp. 825-834, 2015.
Gupta, A., et al., "Community-acquired Clostridium difficile infection: an increasing public health threat", Infection and Drug Resistance, 7, pp. 63-72, 2014.
Abutaleb, N., et al., "Auranofin, at clinically achievable dose, protects mice and prevents recurrence from Clostridioides difficile infection", Scientific Reports, 10:7701, pp. 1-8, 2020.
Abdelkhalek, A., et al., "Antibacterial and antivirulence activities of auranofin against Clostridium difficile", Int J Antimicrob Agents, 53(1), pp. 54-62, 2019.
Shao, X., et al., "Chemical Space Exploration around Thieno[3,2-d]pyrimidin- 4(3H)-one Scaffold Led to a Novel Class of Highly Active Clostridium difficile Inhibitors", J Med Chem, 2019.
Abutaleb, N., et al., "Repurposing the Antiamoebic Drug Diiodohydroxyquinoline for Treatment of Clostridioides difficile Infections", Antimicrob Agents Chemother, 64(6), pp. 11, 2020.
Abdelkhalek, A., et al., "Screening for potent and selective anticlostridial leads among FDA-approved drugs", The Journal of Antibiotics, 73(6), pp. 392-409, 2020.
Pal, R., et al., "Screening of Natural Products and Approved Oncology Drug Libraries for Activity against Clostridioides difficile", Sci Rep, 10:5966, pp. 8, 2020.
Hammad, A., et al., "From Phenylthiazoles to Phenylpyrazoles: Broadening the Antibacterial Spectrum toward Carbapenem-Resistant Bacteria", J Med Chem, 62, pp. 7998-8010, 2019.
Kumar, M., et al., "Action of nitroheterocyclic drugs against Clostridium difficile", International Journal of Antimicrobial Agents, 44, pp. 314-319, 2014.
Asrani, C., et al., "Efficacy and Safety of Metronidazole Versus a Combination of Metronidazole and Diiodohydroxyquinoline for the Treatment of Patients with Intestinal Amebiasis—a Primary-Care Physicians Research Group-Study "Current Therapeutic Research-Clinical and Experimental, 56, pp. 678-683, 1995.
Vendantam, G., et al., "Clostridium difficile infection: toxins and non-toxin virulence factors, and their contributions to disease establishment and host response", Gut Microbes, 3:2: pp. 121-134, 2012.
Locher, H., et al., In Vitro and In Vivo Antibacterial Evaluation of Cadazolid, a New Antibiotic for Treatment of Clostridium difficile Infections Antimicrob Agents Chemother, 58(2): pp. 892-900, 2014.
Kim, S., et al., "The intestinal microbiota: Antibiotics, colonization resistance, and enteric pathogens", Immunological Reviews, 279, pp. 90-105, 2017.
Vardakas, Konstantinos Z. et al., "Treatment failure and recurrent of Clostridium difficile infection following treatment with vancomycin or metronidazole: a systematic review of the evidence," International Journal of Antimicrobial Agents, vol. 40, pp. 1-8, (2012).

(Continued)

*Primary Examiner* — Julie Ha
(74) *Attorney, Agent, or Firm* — Purdue Research Foundation (57) ABSTRACT

A method to treat a patient with a *Clostridium difficile* infection comprising administering a therapeutically effective amount of diiodohydroxyquinoline, with or without one or more anti-infective agents.

6 Claims, 8 Drawing Sheets

(56) References Cited

OTHER PUBLICATIONS

Baines, Simon D. et al., "Antimicrobial Resistance and Reduced Susceptibility in Clostridium difficile: Potential Consequences for Induction, Treatment, and Recurrence of C. difficile Infection," Antibiotics, vol. 4, pp. 267-298, (2015).

Cornely, Oliver A. et al., "Treatment of First Recurrence of Clostridium difficile Infection: Fidaxomicin Versus Vancomycin," Clinical Infectious Diseases, 2CID 012:55 (Suppl 2), (2012).

Hopkins, Roy J. et al., "Treatment of recurrent Clostridium difficile colitis: a narrative review," Gastroenterology Report, vol. 6(1), pp. 21-28 (2018).

\* cited by examiner

DIIODOHYDROXYQUINOLINE FOR THE TREATMENT OF CLOSTRIDIUM DIFFICILE INFECTION

CROSS REFERENCE TO RELATED APPLICATION

This present patent application relates to and claims the priority under 35 U.S.C. § 119(e) to U.S. Provisional Patent Application Ser. No. 62/911,594 filed on Oct. 7, 2019, the content of which is hereby incorporated by reference in its entirety into the present disclosure.

GOVERNMENT SUPPORT CLAUSE

This invention was made with government support under a grant AI130186 awarded by the National Institutes of Health. The government has certain rights in the invention.

TECHNICAL FIELD

The present application relates generally to a method to treat a patient with a bacterial infection by *Clostridium difficile*. Particularly the method compromises the step of administering a therapeutically effective amount of diiodohydroxyquinoline, with or without one or more anti-infective agents, to the patient in need of relief from said infection.

BACKGROUND AND BRIEF SUMMARY OF INVENTION

This section introduces aspects that may help facilitate a better understanding of the disclosure. Accordingly, these statements are to be read in this light and are not to be understood as admissions about what is or is not prior art.

*Clostridium difficile* is the most common hospital-acquired disease in the United States with half million cases annually [1]. *C. difficile* infection (CDI) was associated with over 29,000 deaths in 2011 in USA with a cost exceeding $5 billion annually [2]. CDIs spread rapidly over the past two decades owing to an increase in the number of patients with risk factors for the infection and the emergence of hypervirulent strains (e.g. the 60 North American pulsotype 1 (NAP1) with increased production of lethal toxins A and B [3]. In addition, community-onset CDIs are uprising. CDI is being increasingly recognized in the community, in younger individuals and in patients lacking the CDI traditional risk factors for, such as hospitalization, age and antibiotic exposure [4, 5]. Fidaxomicin was the only new antibiotic that has been approved in the last 30 years for the treatment of CDIs. Currently, only two drugs are recommended for treatment of CDI (vancomycin and fidaxomicin). Metronidazole, which was previously recommended as a first-line therapeutic option for CDIs in adults, is no longer recommended for treatment of severe CDI and is restricted to be used when patients are unable to obtain or be treated with vancomycin or fidaxomicin [6]. Nevertheless, the available treatment options are inadequate in efficacy and associated with high recurrence rates [7-9]. Moreover, resistance or reduced susceptibility to these antibiotics is emerging [8, 9]. Furthermore, the treatment outcomes of fidaxomicin in the recurrent CDI is not satisfactory [10]. Taken together, there is a critical and an unmet need for new anti-clostridial drugs with improved treatment outcomes.

BRIEF DESCRIPTION OF THE DRAWINGS

The above and other objects, features, and advantages of the present invention will become more apparent when taken in conjunction with the following drawings, and wherein:

FIG. 6 shows toxin inhibition activity of diiodohydroxyquinoline (DIHQ) and control anticlostridial drugs; fidaxomicin, metronidazole and vancomycin against *C. difficile* ATCC BAA-1870. Drugs, at concentrations of 0.25×MIC and 0.5×MIC were incubated with *C. difficile* ATCC BAA-1870 (a hypervirulent toxigenic strain). The bacterial counts (represented by gray bars) were determined for each sample, and the toxin levels (represented by the connected lines) were assessed in the supernatant using enzyme linked immunosorbent assay (ELISA). Error bars represent standard deviation values from triplicate samples for each treatment. The data were analyzed via one-way ANOVA with post hoc Dunnett's test for multiple comparisons. Asterisks (*) denote statistical significant difference between the results obtained in fidaxomicin- or DIHQ-treated samples as compared to the untreated samples.

FIG. 7 shows toxin inhibition activity of diiodohydroxyquinoline (DIHQ) and control anticlostridial drugs; fidaxomicin, metronidazole and vancomycin against *C. difficile* ATCC 43255. Drugs, at concentrations of 0.25×MIC and 0.5×MIC were incubated with *C. difficile* ATCC 43255 (a hypervirulent toxigenic strain). The bacterial counts (represented by gray bars) were determined for each sample, and the toxin levels (represented by the connected lines) were assessed in the supernatant using enzyme linked immunosorbent assay (ELISA). Error bars represent standard deviation values from triplicate samples for each treatment. The data were analyzed via one-way ANOVA with post hoc Dunnett's test for multiple comparisons. Asterisks (*) denote statistical significant difference between the results obtained with fidaxomicin- or DIHQ-treated samples as compared to the untreated samples.

FIG. 8 shows toxin inhibition activity of diiodohydroxyquinoline (DIHQ) and control anticlostridial drugs: fidaxomicin, metronidazole and vancomycin against *C. difficile* ATCC NR-49277. Drugs, at concentrations of 0.25×MIC and 0.5×MIC were incubated with *C. difficile* NR-49277 (a hypervirulent toxigenic strain). The bacterial counts (represented by gray bars) were determined for each sample, and the toxin levels (represented by the connected lines) were assessed in the supernatant using enzyme linked immunosorbent assay (ELISA). Error bars represent standard deviation values from triplicate samples for each treatment. The data were analyzed via one-way ANOVA with post hoc Dunnett's test for multiple comparisons.
Asterisks (*) denote statistical significant difference between the results obtained in fidaxomicin- or DIHQ-treated samples as compared to the untreated samples.

DETAILED DESCRIPTION

For the purposes of promoting and understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

The present application relates generally to a method to treat a patient with a bacterial infection by *Clostridium difficile*. Particularly the method compromises the step of administering a therapeutically effective amount of diiodohydroxyquinoline, with or without one or more anti-infective agents, to the patient in need of relief from said infection.

In some illustrative embodiments, the present invention relates to a method for treating a patient of a bacterial infection compromising the step of administering a therapeutically effective amount of 5,7-diiodoquinolin-8-ol (a.k.a. diiodohydroxyquinoline) to the patient in need of relief from said infection.

In some illustrative embodiments, the present invention relates to a method for treating a patient of a bacterial infection caused by *Clostridium difficile* compromising the step of administering a therapeutically effective amount of 5,7-diiodoquinolin-8-ol to the patient in need of relief from said infection.

In some illustrative embodiments, the present invention relates to a method for treating a patient of a bacterial infection caused by *Clostridium difficile* compromising the step of administering a therapeutically effective amount of 5,7-diiodoquinolin-8-ol to the patient in need of relief from said infection, wherein said 5,7-diiodoquinolin-8-ol is administered orally.

In some illustrative embodiments, the present invention relates to a method for treating a patient of a bacterial infection caused by *Clostridium difficile* compromising the step of administering a therapeutically effective amount of 5,7-diiodoquinolin-8-ol, together with one or more other antibiotics, to the patient in need of relief from said infection, A method for treating a patient infected by *Clostridium difficile* comprising the step of administering a therapeutically effective amount of 5,7-diiodoquinolin-8-ol, together with one or more pharmaceutically acceptable carriers, diluents, and excipients, to the patient in need of relief from said infection.

In some illustrative embodiments, the present invention relates to a method for treating a patient of a bacterial infection caused by *Clostridium difficile* compromising the step of administering a therapeutically effective amount of 5,7-diiodoquinolin-8-ol, and one or more other antibiotics, together with one or more pharmaceutically acceptable carriers, diluents, and excipients, to the patient in need of relief from said infection.

In some illustrative embodiments, the present invention relates to a method for treating a patient of a bacterial infection caused by *Clostridium difficile* compromising the step of administering a therapeutically effective amount of 5,7-diiodoquinolin-8-ol, and an anti-infective agent selected from the group consisting of metronidazole, vancomycin and fidaxomicin, together with one or more pharmaceutically acceptable carriers, diluents, and excipients, to the patient in need of relief from said infection.

In some illustrative embodiments, the present invention relates to a method for treating a patient of a bacterial infection caused by *Clostridium difficile* compromising the step of administering a therapeutically effective amount of 5,7-diiodoquinolin-8-ol, and an anti-infective agent selected from the group consisting of metronidazole, vancomycin and fidaxomicin, together with one or more pharmaceutically acceptable carriers, diluents, and excipients, to the patient in need of relief from said infection, wherein 5,7-diiodoquinolin-8-ol and an anti-infective agent are combined and administered together.

In some illustrative embodiments, the present invention relates to a method for treating a patient of a bacterial infection caused by *Clostridium difficile* compromising the step of administering a therapeutically effective amount of 5,7-diiodoquinolin-8-ol, and an anti-infective agent selected from the group consisting of metronidazole, vancomycin and fidaxomicin, together with one or more pharmaceutically acceptable carriers, diluents, and excipients, to the patient in need of relief from said infection, wherein 5,7-diiodoquinolin-8-ol and an anti-infective agent are administered separately.

In some illustrative embodiments, the present invention relates to a method for treating a patient of a bacterial infection caused by *Clostridium difficile* compromising the step of administering a therapeutically effective amount of 5,7-diiodoquinolin-8-ol, and one or more other antibiotics selected from the group consisting of metronidazole, vancomycin and fidaxomicin, together with one or more pharmaceutically acceptable carriers, diluents, and excipients, to the patient in need of relief from said infection, wherein said 5,7-diiodoquinolin-8-ol is administered orally or topically.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients as disclosed herein, wherein said anti-infective agent is metronidazole, vancomycin or fidaxomicin.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients as disclosed herein, wherein said 5,7-diiodoquinolin-8-ol is administered orally.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients as disclosed herein, wherein said 5,7-diiodoquinolin-8-ol is administered topically.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients as disclosed herein, wherein said 5,7-diiodoquinolin-8-ol and one or more anti-infective agents are combined and administered at the same time.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients as disclosed herein, wherein said 5,7-diiodoquinolin-8-ol and one or more anti-infective agents are administered separately.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients as disclosed herein, wherein said 5,7-diiodoquinolin-8-ol and one or more anti-infective agents are administered consequentially.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients as disclosed herein, wherein said 5,7-diiodoquinolin-8-ol and one or more anti-infective agents are administered orally.

In some other illustrative embodiments, the present invention relates to a pharmaceutical composition for the treatment of infections caused by *Clostridium difficile* comprising therapeutically effective amount of 5,7-diiodoquinolin-8-ol, together with one or more anti-infective agents and one or more pharmaceutically acceptable carriers, diluents, and excipients as disclosed herein, wherein said 5,7-diiodoquinolin-8-ol and one or more anti-infective agents are administered topically.

The term "patient" includes human and non-human animals such as companion animals (dogs and cats and the like) and livestock animals. Livestock animals are animals raised for food production. The patient to be treated is preferably a mammal, in particular a human being.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffered solutions; and (21) other nontoxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

It is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosage may be single or divided, and may be administered according to a wide variety of dosing protocols, including q.d., b.i.d., t.i.d., or even every other day, once a week, once a month, and the like. In each case the therapeutically effective amount described herein corresponds to the instance of administration, or alternatively to the total daily, weekly, or monthly dose.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., Cancer Chemother. Rep. 1966, 50 (4), 219, the disclosure of which is incorporated herein by reference. Body surface area may be approximately determined from patient height and weight (see, e.g., Scientific Tables, Geigy Pharmaceuticals, Ardley, New York, pages 537-538 (1970)). A therapeutically effective amount of the compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of compound per patient body weight. It is appreciated that effective doses may also vary depending on the route of administration, optional excipient usage, and the possibility of co-usage of the compound with other conventional and non-conventional therapeutic treatments, including other anti-tumor agents, radiation therapy, and the like.

The present invention may be better understood in light of the following non-limiting compound examples and method examples.

Drug discovery is a time-consuming and expensive venture. Developing a new drug can take 10 to 15 years from early stage discovery to receiving regulatory approval and can cost more than two billion dollars [11]. Repurposing existing FDA approved drugs for new indications is a promising approach for drug discovery. Advantageously, FDA approved drugs are extensively investigated in terms of the safety profile, pharmacodynamics and pharmacokinetics which will reduce both the time and cost associated with drug development [12-22]. Antiparasitic drugs are a class of medications indicated for the treatment of parasitic diseases, such as those caused by helminths, amoeba, and protozoa [23]. Most of antiparasitic drugs are administered orally and poorly absorbed from the gastrointestinal tract (GIT), a character that is highly desirable for targeting intestinal pathogens, like *C. difficile*.

Consequently, in this study, we screened a library of antiparasitic drugs to search for activity against *C. difficile*. We were interested in finding a drug which can inhibit *C. difficile* with the advantage of being less absorbed from GIT (Table 1). Our screen identified diiodohydroxyquinoline (DIHQ), a drug that exhibited a potent activity against *C. difficile*. DIHQ is used for the treatment of amoebiasis [24]. It is poorly absorbed from the GIT and is used as a luminal amebicide. In the current study, we evaluated DIHQ as a promising candidate for treatment of CDI. It possesses potent antibacterial activity against a wide panel of *C. difficile* strains, in a clinically achievable range. Additionally, it is capable of inhibiting *C. difficile* toxin production and spore formation. Moreover, it interacted synergistically with the current therapeutics for *C. difficile* (vancomycin and metronidazole) against clinical *C. difficile* isolates, prove highly efficacious killing of hypervirulent strains of *C. difficile*; and highly specific towards *C. difficile* with minimal activity against the protective gut microbiome. Taken together, the characteristics of diiodohydroxyquinoline may offer a safe, effective, and quick supplement to the current approaches for treating *C. difficile*.

Materials and Methods:

Chemicals, Media and Bacterial Strains.

Diiodohydroxyquinoline (DIHQ), albendazole, mebendazole (Tokyo Chemical Industry, OR), praziquantel, cambendazole, ricobendazole, thiabendazole, fidaxomicin (Cayman Chemicals, MI), paromomycin sulfate, metronidazole (Alfa Aesar, MA), pyrantel pamoate (Acros Organics, NJ), pyrimethamine (MP Biomedicals, OH), and vancomycin hydrochloride (Gold Biotechnology, St. Louis, MO) were purchased from commercial vendors. Brain heart infusion broth and lactobacilli MRS broth were purchased from Becton, Dickinson and Company (Cockeysville, MD). Phosphate buffered saline was purchased from Fisher Scientific (Waltham, MA). Yeast extract, L-cysteine, vitamin K and hemin were obtained from Sigma-Aldrich (St. Louis, MO). *C. difficile* isolates were obtained from the American Type Culture Collection (ATCC) and the Biodefense and Emerging Infections Research Resources Repository (BEI Resources).

Screening a Library of Antiparasitic Drugs Against *Clostridium difficile*:

The minimum inhibitory concentrations (MICs) of the antiparasitic drugs library and control antibiotics (vancomycin and metronidazole) was determined using the broth microdilution method against clinical strains of *C. difficile*, as described previously [18, 25-29]. *C. difficile* strains were grown anaerobically on brain heart infusion supplemented (BHIS) agar plates at 37° C. for 48 hours. Afterwards, a bacterial solution equivalent to 0.5 McFarland standard was prepared and diluted in (BHIS) broth to achieve a bacterial concentration of about $5 \times 10^5$ CFU/mL. Drugs were added and serially diluted along the plates. Plates were then, incubated anaerobically at 37° C. for 48 hours. MICs reported in Table (1) are the minimum concentrations of the drugs that could completely suppress the visual growth of bacteria.

Antibacterial activity of Diiodohydroxyquinoline against a wide panel of *Clostridium difficile* strains. The MICs of diiodohydroxyquinoline and control antibiotics (vancomycin, metronidazole and fidaxomicin) was determined using the broth microdilution method against a panel of clinical strains of *C. difficile* as described previously [18, 25-29].

MICs reported in Table (2) are the minimum concentrations of the drugs that completely suppressed the visual growth of bacteria. $MIC_{50}$ and $MIC_{90}$ are the minimum concentration of each agent that inhibited growth of 50% and 90% of the tested isolates, respectively. The minimum bactericidal concentration (MBC) of these drugs was tested by plating 5 µL from wells with no growth onto BHIS agar plates. The MBC was categorized as the lowest concentration that reduced bacterial growth by 99.9% $MIC_{50}$ and $MIC_{90}$ are the minimum concentration of each agent that inhibited the growth of 50% and 90% of the tested isolates, respectively. The minimum bactericidal concentration (MBC) of these drugs was tested by plating 5 µL from wells with no growth onto BHIS agar plates. The MBC was categorized as the lowest concentration that reduced bacterial growth by 99.9% [29-31].

Time kill kinetics assay. In order to examine the killing kinetics of DIHQ, a time kill kinetics assay was performed against *Clostridium difficile* ATCC BAA 1870 and *C. difficile* NR-49277 as described previously [32]. *C. difficile* cells in logarithmic growth phase were diluted to ~$10^6$ CFU/mL and exposed to concentrations equivalent to 5×MIC (in triplicate) of DIHQ, metronidazole or vancomycin in BHIS broth. Aliquots were collected from each treatment after 0, 4, 6, 8, 12, and 24 hours of incubation at 37° C. and subsequently serially diluted and plated for viable CFU/mL determination.

Interactions between diiodohydroxyquinoline and the anticlostridial drugs (metronidazole and vancomycin) against *Clostridium difficile* clinical isolates. To evaluate the interactions between diiodohydroxyquinoline and the anticlostridial drugs (vancomycin and metronidazole) against *C. difficile* clinical isolates, a standard checkerboard assay was utilized as described in previous studies [33, 34]. The fractional inhibitory concentration index (ΣFIC) was calculated for each interaction. Interactions where the ΣFIC index was ≤0.5 were categorized as synergistic (SYN). An ΣFIC value of >0.5-1.25 was considered additive (ADD), and ΣFIC value of >1.25-4 was considered indifference. ΣFIC values>4 were categorized as antagonistic [35].

The Effect of Diiodohydroxyquinoline on *C. difficile* Spore Formation

The spore inhibition assay was performed as described in previous reports [18, 36] to investigate the effect of diiodohydroxyquinoline on *C. difficile* spore formation. Briefly, Afterwards, the bacterial suspension was split into microcentrifuge tubes and drugs were added (in triplicates) at concentrations equal to ½×MIC or 1×MIC. Tubes were then, incubated anaerobically for five days at 37° C. Thereafter, an aliquot from each tube was diluted and plated on BHIS agar plates supplemented with 0.1% taurocholic acid, to count the total bacterial counts (vegetative bacteria+spores). The remaining solution was centrifuged, and the pellet was suspended in PBS, stored overnight at 4° C., and subsequently shock-heated at 70° C. for 30 minutes to kill the vegetative cells. The resulting solution was serially diluted and plated to determine the heat-resistant spore counts. Spore inhibition assay was performed as described in previous reports [18, 36] to investigate the effect of DIHQ on *C. difficile* spore formation. Briefly, log-phase cultures of *C. difficile* strains (ATCC BAA-1870, ATCC 43255, and NR-49277) were diluted in BHIS to an initial density of ~$10^6$ CFU/mL. Afterwards, the bacterial suspension was split in small tubes and the drugs were added (in triplicates) at concentrations equal to ½×MIC or 1×MIC. Tubes were then incubated anaerobically for 5 days at 37° C. After that, an aliquot from each tube was diluted and plated on BHIS agar plates supplemented with 0.1% taurocholic acid, to count the total bacterial count (vegetative bacteria+spores). The remaining solution was centrifuged, and the pellet was suspended in PBS and stored overnight at 4° C. then shock heated at 70° C. for 30 minutes to kill the vegetative cells. The resulting solution was serially diluted and plated to determine the heat-resistant spore counts.

The Effect of Diiodohydroxyquinoline on *C. difficile* Toxin Production

To investigate DIHQs toxin production inhibitory activity, toxin A and toxin B levels were measured as described previously [18, 37]. Briefly, drug concentrations equivalent to ¼×MIC and ½×MIC were added (in triplicates) to late exponential phase cultures of a hypervirulent toxigenic *C. difficile* strains (*C. difficile* ATCC BAA-1870, *C. difficile* ATCC 43255 and *C. difficile* NR-49277), and incubated anaerobically at 37° C. for 8 hours. An aliquot from each tube was diluted and plated on BHIS agar plates and incubated anaerobically at 37° C. for 24 hours to detect the bacterial count. The total concentration of *C. difficile* toxin A and B was measured in the supernatant of each tube using enzyme linked immunosorbent assay (ELISA) kit (tgc BIOMICS, Dunwoody, GA) following the manufacturer's instructions. The ($OD_{450}$-$OD_{620}$) values, corresponding to the toxin concentration, were measured for DIHQ and control drugs.

In vitro antimicrobial evaluation of diiodohydroxyquinoline against normal microflora. The broth microdilution assay was utilized to determine the MICs of DIHQ and control antibiotics against commensal organisms that compose he human gut microflora, as described elsewhere [38, 39]. A bacterial solution equivalent to 0.5 McFarland standard was prepared and diluted in BHIS broth (for *Bifidobacterium* and *Bacteroides*) or in MRS broth (for *Lactobacillus*) to achieve a bacterial concentration of about 5×$10^5$ CFU/mL. Then, drugs were added and serially diluted along the plates. Plates were incubated for 48 hours at 37° C. before recording the MIC values as observed visually.

Screening a Library of Antiparasitic Drugs Against *Clostridium difficile*:

A small panel of poorly absorbed antiparasitic drugs was initially screened against 2 clinical *C. difficile* strains to investigate their anticlostridial activity. As shown in Table 1, the antiparasitic drugs were inactive (up to 128 µg/mL) against both *C. difficile* strains, with the exception of DIHQ. DIHQ exhibited a potent activity against both tested *C. difficile* where it inhibited their growth at concentrations ranging from 0.5 to 1 µg/mL. Interestingly, it was as effective as vancomycin; the drug of choice of treatment of *C. difficile* infections.

Antibacterial Activity of Diiodohydroxyquinoline Against a Panel of Clinical *C. difficile* Strains The anticlostridial activity of DIHQ was evaluated against a large panel of *C. difficile* clinical isolates. As shown in Table 2, DIHQ inhibited growth of the 38 tested *C. difficile* strains at concentrations ranging from 0.06-2 µg/mL. It was capable of inhibiting 50% of the tested isolates ($MIC_{50}$) at a concentration of 0.5 µg/mL and inhibited 90% of the isolates ($MIC_{90}$) at a concentration of 2 µg/mL. Furthermore, its MIC values was comparable to the MIC values of vancomycin, the drug of choice for treatment of severe *C. difficile* infections (CDI) where it inhibited 50% and 90% of the strains at 0.5 µg/mL and 1 µg/mL, respectively. Metronidazole, the drug of choice for anaerobic bacterial infections [40], was effective at a range of 0.06-0.5 µg/mL with $MIC_{50}$ and $MIC_{90}$ values of 0.125 µg/mL and 0.25 µg/mL respectively. On the other hand, fidaxomicin inhibited 50% and 90% of the tested strains at concentrations of 0.015 µg/mL and 0.06 µg/mL respectively.

TABLE 1

Initial screening (MICs in µg/mL) of the antiparasitic drugs against *C. difficile* ATCC BAA-1870 and *C. difficile* ATCC 43255

|  | Bacterial Strains | |
| --- | --- | --- |
| Drugs/Control antibiotics | *C. difficile* ATCC BAA 1870 | *C. difficile* ATCC 43255 |
| Albendazole | >128 | >128 |
| Mebendazole | >128 | >128 |
| Ricobendazole | >128 | >128 |
| Thiabendazole | >128 | >128 |
| Cambendazole | >128 | >128 |
| Praziquantel | >128 | >128 |
| Pyrantel Pamoate | >128 | >128 |
| Paromomycin | >128 | >128 |
| Pyrimethamine | >128 | >128 |
| DIHQ | 1 | 0.5 |
| Vancomycin | 1 | 1 |
| Metronidazole | 0.125 | 0.25 |

To determine if DIHQ exhibits bacteriostatic or bactericidal activity against *C. difficile*, we also determined the minimum bactericidal concentrations (MBCs) against all 38 isolates. The MBC values for DIHQ were equal to or two-fold higher than the corresponding MIC values for all 39 isolates indicating that DIHQ is a bactericidal agent. A similar result was observed for vancomycin and metronidazole.

TABLE 2

The minimum inhibitory concentrations (MICs in µg/mL) and minimum bactericidal concentrations (MBCs in µg/mL) of DIHQ and control drugs against clinical isolates of *C. difficile*.

|  | Drugs | | | | | | | |
| --- | --- | --- | --- | --- | --- | --- | --- | --- |
|  | DIHQ | | Vancomycin | | Metronidazole | | Fidaxomicin | |
| *C. difficile* Strains | MIC | MBC | MIC | MBC | MIC | MBC | MIC | MBC |
| ATCC BAA-1870 | 1 | 1 | 1 | 1 | 0.125 | 0.125 | 0.03 | 0.03 |
| ATCC 43255 | 0.5 | 0.5 | 1 | 1 | 0.25 | 0.25 | 0.015 | 0.015 |
| ATCC 43598 | 1 | 1 | 1 | 1 | 0.125 | 0.125 | 0.015 | 0.015 |
| ATCC 9689 | 0.125 | 0.25 | 0.5 | 1 | 0.125 | 0.25 | 0.03 | 0.03 |
| ATCC 1801 | 2 | 4 | 1 | 1 | 0.25 | 0.25 | 0.06 | 0.125 |
| ATCC 700057 | 0.5 | 0.5 | 0.5 | 0.5 | 0.125 | 0.125 | 0.007 | 0.007 |
| I1 | 1 | 1 | 1 | 1 | 0.125 | 0.125 | 0.007 | 0.007 |
| I2 | 2 | 2 | 1 | 1 | 0.125 | 0.125 | 0.007 | 0.007 |
| I4 | 1 | 1 | 0.5 | 0.5 | 0.125 | 0.125 | 0.015 | 0.015 |
| I6 | 0.5 | 0.5 | 0.5 | 0.5 | 0.25 | 0.25 | 0.06 | 0.06 |
| I9 | 0.06 | 0.06 | 0.5 | 0.5 | 0.06 | 0.06 | 0.03 | 0.03 |
| I10 | 1 | 1 | 0.5 | 1 | 0.25 | 0.25 | 0.015 | 0.03 |
| I11 | 1 | 1 | 1 | 1 | 0.25 | 0.25 | 0.015 | 0.015 |
| I13 | 2 | 2 | 1 | 1 | 0.25 | 0.5 | 0.03 | 0.03 |
| P1 | 0.5 | 0.5 | 0.5 | 0.5 | 0.125 | 0.125 | 0.003 | 0.007 |
| P2 | 0.25 | 0.25 | 1 | 1 | 0.125 | 0.25 | 0.03 | 0.03 |
| P3 | 2 | 2 | 1 | 1 | 0.25 | 0.25 | 0.015 | 0.03 |
| P5 | 2 | 4 | 0.5 | 0.5 | 0.25 | 0.25 | 0.03 | 0.03 |
| P6 | 0.5 | 0.5 | 1 | 1 | 0.25 | 0.25 | 0.003 | 0.003 |
| P7 | 0.5 | 0.5 | 0.5 | 0.5 | 0.125 | 0.125 | 0.06 | 0.06 |
| P8 | 0.125 | 0.125 | 1 | 1 | 0.125 | 0.125 | 0.015 | 0.015 |
| P11 | 0.25 | 0.25 | 1 | 1 | 0.125 | 0.25 | 0.03 | 0.03 |
| P13 | 0.5 | 0.5 | 0.5 | 0.5 | 0.125 | 0.25 | 0.015 | 0.015 |
| P15 | 1 | 1 | 1 | 1 | 0.25 | 0.25 | 0.06 | 0.06 |
| P19 | 0.5 | 1 | 1 | 1 | 0.25 | 0.25 | 0.03 | 0.06 |
| P20 | 1 | 1 | 1 | 1 | 0.25 | 0.25 | 0.015 | 0.015 |
| P24 | 1 | 2 | 0.5 | 0.5 | 0.125 | 0.25 | 0.015 | 0.03 |
| P30 | 0.5 | 0.5 | 0.5 | 0.5 | 0.5 | 0.5 | 0.007 | 0.007 |
| HM-89 | 1 | 1 | 1 | 1 | 0.125 | 0.125 | 0.03 | 0.03 |
| HM-745 | 1 | 1 | 1 | 1 | 0.5 | 0.5 | 0.06 | 0.125 |
| NR-49277 | 0.5 | 0.5 | 1 | 1 | 0.125 | 0.125 | 0.03 | 0.03 |
| NR-49278 | 0.25 | 0.5 | 0.25 | 0.5 | 0.25 | 0.5 | 0.007 | 0.015 |
| NR-49281 | 0.25 | 0.25 | 0.25 | 0.25 | 0.125 | 0.125 | 0.007 | 0.007 |
| NR-49284 | 0.125 | 0.125 | 0.25 | 0.5 | 0.125 | 0.125 | 0.015 | 0.015 |
| NR-49285 | 1 | 1 | 0.5 | 0.5 | 0.25 | 0.5 | 0.015 | 0.03 |
| NR-49286 | 0.25 | 0.5 | 0.25 | 0.5 | 0.125 | 0.125 | 0.007 | 0.015 |
| NR-49288 | 0.25 | 0.5 | 0.5 | 1 | 0.25 | 0.25 | 0.007 | 0.015 |
| NR-49290 | 0.25 | 0.5 | 0.5 | 1 | 0.125 | 0.25 | 0.015 | 0.015 |
| $MIC_{50}$ | 0.5 |  | 0.5 |  | 0.125 |  | 0.015 |  |
| $MIC_{90}$ | 2 |  | 1 |  | 0.25 |  | 0.06 |  |

Figure 1:
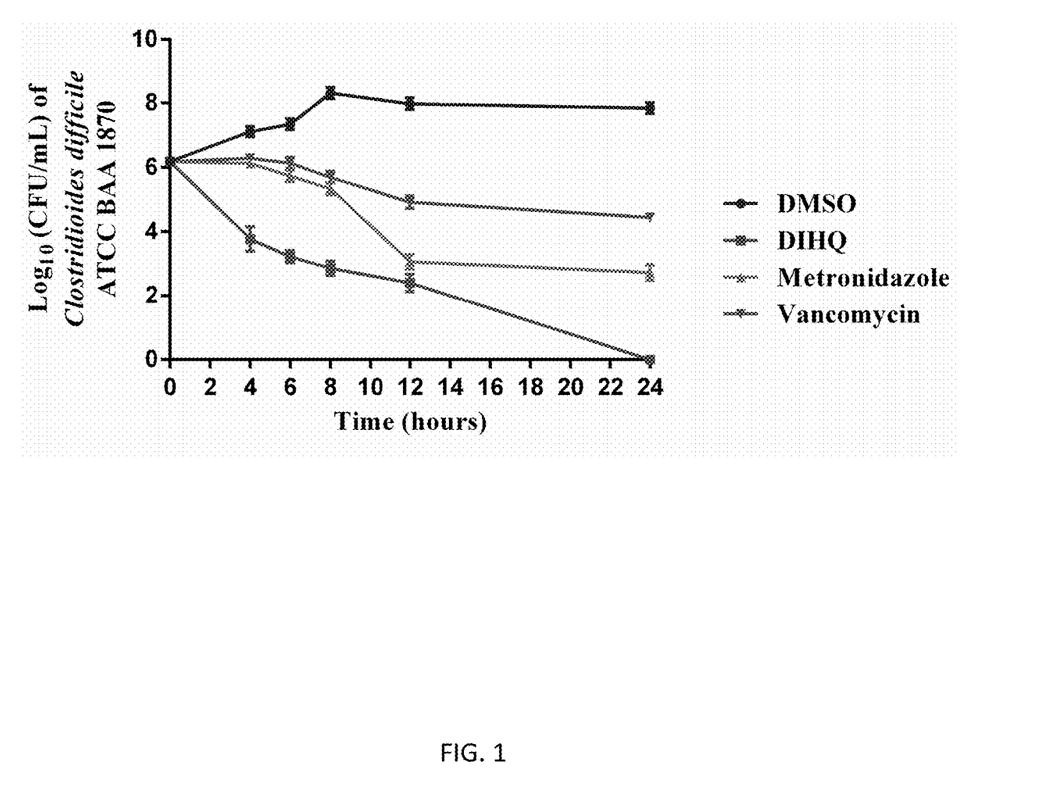
FIG. 1 depicts time-kill kinetics analysis of diiodohydroxyquinoline (DIHQ), metronidazole and vancomycin (at 5×MIC) against *Clostridium difficile* ATCC BAA-1870 over a 24-hours incubation period at 37° C. DMSO served as a negative control. The error bars represent standard deviation values obtained from triplicate samples used for each test agent.

Time Kill Kinetics Assay of Diiodohydroxyquinoline and the Anticlostridial Drugs To confirm the bactericidal activity of DIHQ against *C. difficile*, we examined how rapidly it reduced the burden of a high *C. difficile* inoculum via a time-kill assay. In coincidence with the results obtained in MBC experiment, DIHQ exerted a rapid bactericidal activity against *C. difficile* ATCC BAA-1870. DIHQ required only six hours to generate a 3-$\log_{10}$ reduction in CFU/mL and completely eradicated the bacteria (below the detection limit, 100 CFU/mL), within 24 hours (FIG. 1). Remarkably, DIHQ was superior to both metronidazole and vancomycin in the in vitro time-kill assay. Metronidazole produced a 3-$\log_{10}$ reduction in *C. difficile* CFU/mL after 12 hours. Vancomycin exhibited slow reduction of *C. difficile* count and only reduced the bacterial burden by 1.7-$\log_{10}$ CFU/mL within 24 hours (FIG. 1).

Figure 2:
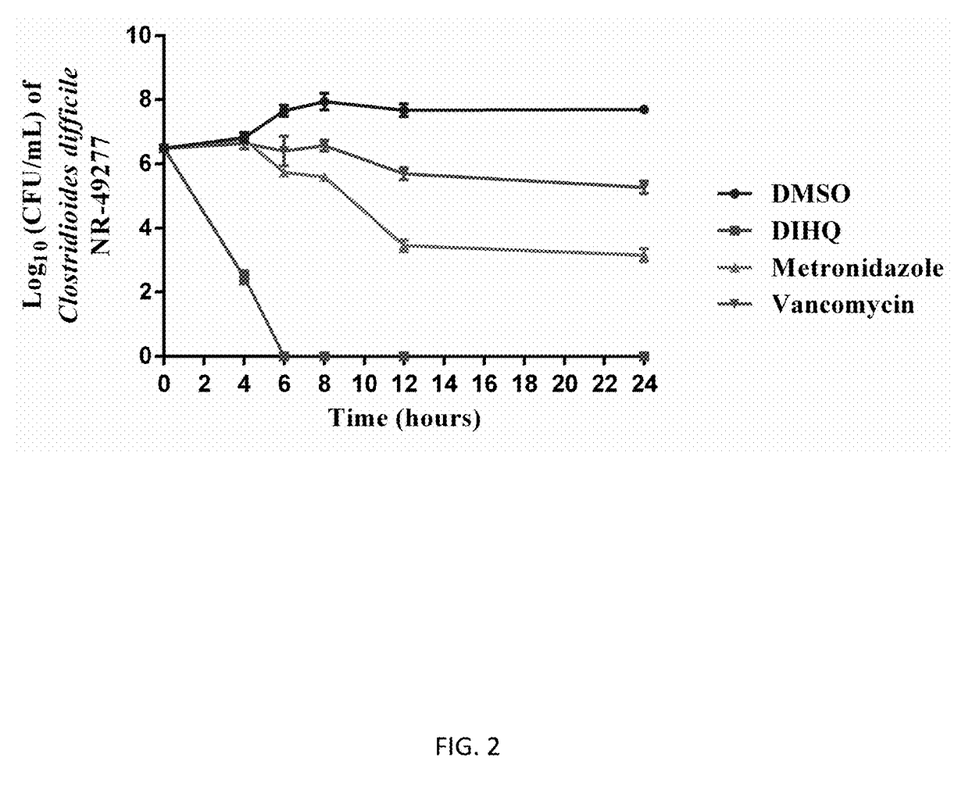
FIG. 2 depicts time-kill kinetics analysis of diiodohydroxyquinoline (DIHQ), metronidazole and vancomycin (at 5×MIC) against *Clostridium difficile* NR-49277 over a 24-hours incubation period at 37° C. DMSO served as a negative control. The error bars represent standard deviation values obtained from triplicate samples used for each test agent.

In addition, DIHQ exerted a rapid bactericidal activity against *C. difficile* NR-49277. It required only 4 hours to generate more than 3-login reduction in CFU/mL and completely eradicated the bacteria (below the detection limit, 100 CFU/mL), within 6 hours (FIG. 2). Interestingly, DIHQ was superior to both metronidazole and vancomycin in reducing the burden of *C. difficile* NR-49277. Metronidazole produced a 3-$\log_{10}$ reduction in *C. difficile* CFU/mL after 12 hours while vancomycin reduced the bacterial burden by 1.22-$\log_{10}$ CFU/mL within 24 hours.

Interactions Between Diiodohydroxyquinoline and Anticlostridial Drugs (Metronidazole and Vancomycin) Against *Clostridium difficile* Clinical Isolates Combination therapy has become a standard in several diseases. This strategy is now often used in the healthcare setting to gain the advantages of combined drugs such as different mechanisms of action, lower toxicity, potential synergism and less probability of development of resistance to both agents [41, 42]. It represents a promising approach in indications of unmet medical need. Combination therapy was investigated in treatment of CDI. A combination of vancomycin+rifampicin was found to be effective in resolving CDI and decreasing the rate of recurrence [43]. Vancomycin/metronidazole combination was also, proposed for CDI although it was as effective as vancomycin alone [44]. Nevertheless, combination therapy is a promising strategy for treating CDI, particularly for severe infections where one agent may not be effective. It was reported previously that DIHQ exhibited a potent synergistic interaction with metronidazole in treatment of amoebiasis [45]. In this context, we investigated the effects of a combination of DIHQ with either vancomycin or metronidazole in order to provide evidence of a significant superiority compared to the single drugs (Tables 3 and 4). As depicted in Tables 3 and 4, DIHQ exhibited a potent synergistic interaction with metronidazole more frequently than with vancomycin in coincidence with previous studies against other microbes [45]. Combined with metronidazole, DIHQ showed a synergistic relationship against 7 out of 9 tested strains with fractional inhibitory concentration (FIC) indices that ranged from 0.18 to 0.37 (Table 3). On the other hand, when it was combined with vancomycin, it interacted synergistically in 5 out of 9 tested strains with FIC indices range similar to that of metronidazole (Table 4).

TABLE 3

Interactions between DIHQ and metronidazole against *C. difficile* clinical isolates.

| | MICs (μg/ml) | | | | | |
| --- | --- | --- | --- | --- | --- | --- |
| | Metronidazole | | DIHQ | | | |
| *C. difficile* strains | Alone | Combined with DIHQ | Alone | Combined with metronidazole | [1]ΣFIC Index | Interpretation* |
| ATCC BAA-1870 | 0.125 | 0.015 | 1 | 0.125 | 0.25 | SYN |
| ATCC 43255 | 0.125 | 0.015 | 1 | 0.25 | 0.375 | SYN |
| ATCC 9689 | 0.25 | 0.03 | 0.125 | 0.06 | 0.62 | ADD |
| ATCC 1801 | 0.25 | 0.03 | 4 | 1 | 0.37 | SYN |
| P11 | 0.25 | 0.03 | 0.5 | 0.125 | 0.37 | SYN |
| P19 | 0.5 | 0.06 | 0.5 | 0.06 | 0.24 | SYN |
| P30 | 0.5 | 0.06 | 1 | 0.06 | 0.185 | SYN |
| I6 | 0.25 | 0.03 | 2 | 0.125 | 0.188 | SYN |
| I9 | 0.125 | 0.015 | 0.06 | 0.06 | 1.125 | ADD |

Figure 3:
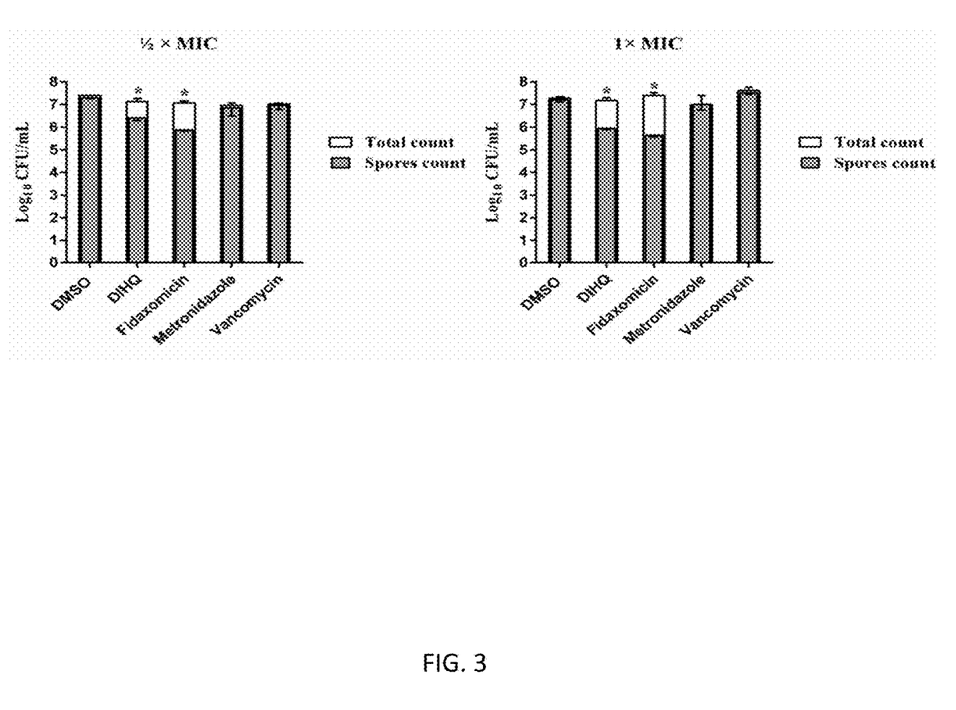
FIG. 3 shows spore inhibition of activity of diiodohydroxyquinoline (DIHQ) against *C. difficile* compared to the control anti-clostridial drugs; fidaxomicin, vancomycin and metronidazole against *C. difficile* ATCC BAA-1870. Drugs at a concentration of 0.5×MIC and 1×MIC were incubated with bacteria for five days followed by serial dilution and plating to count both total bacterial count and spores count. DMSO (solvent of the drugs) served as a negative control. Error bars represent standard deviation values from triplicate samples for each treatment.

[1]ΣFIC; fractional inhibitory concentration
*ΣFIC index ≤0.5 is considered synergistic (SYN);
ΣFIC index >0.5 – 1.25 is considered additive (ADD);
ΣFIC index >1.25 – 4 is considered indifference (IND);
ΣFIC index >4 is considered antagonistic The Effect of Diiodohydroxyquinoline Against *C. difficile* Spore Formation Spore formation is a key virulence factor of *C. difficile*. The higher the ability of a strain to form spores, the more virulent and the more resistant to the disinfection procedures is it. Spore formation is a key virulence factor of *C. difficile* that is responsible for both the rapid spread and high recurrence rate of infection [46, 47]. Persistent *C. difficile* spores can germinate in the intestine, after the end of the treatment course, leading to the recurrence of infection [48]. We investigated the efficacy of DIHQ to inhibit *C. difficile* ATCC BAA-1870 spores formation. As shown in FIG. 3, DIHQ-treated bacteria displayed a significantly reduced spore count by nearly 0.74-$\log_{10}$ and 1.24-$\log_{10}$ at ½×MIC and 1×MIC, respectively. Fidaxomicin, which is known to be capable of inhibiting spore formation [49], significantly reduced *C. difficile* spore formation by nearly 1.02-$\log_{10}$ reduction (at ½×MIC) and 1.8-$\log_{10}$ reduction (at 1×MIC). On the other hand, almost no reduction in the spore count was observed when vegetative cells were exposed to either vancomycin or metronidazole (FIG. 3).

TABLE 4

Interactions between diiodohydroxyquinoline and vancomycin against *C. difficile* clinical isolates.

| | MIC (μg/ml) | | | | | |
| --- | --- | --- | --- | --- | --- | --- |
| | Vancomycin | | DIHQ | | | |
| *C. difficile* strains | Alone | Combined with DIHQ | Alone | Combined with vancomycin | [1]ΣFIC Index | Interpretation* |
| ATCC BAA-1870 | 1 | 0.125 | 1 | 0.06 | 0.185 | SYN |
| ATCC 43255 | 1 | 0.125 | 1 | 0.125 | 0.25 | SYN |
| ATCC 9689 | 1 | 0.125 | 0.125 | 0.06 | 0.625 | ADD |
| ATCC 1801 | 0.5 | 0.06 | 4 | 2 | 0.625 | ADD |
| P11 | 1 | 0.125 | 0.5 | 0.5 | 1.125 | ADD |
| P19 | 1 | 0.125 | 0.5 | 0.125 | 0.375 | SYN |
| P30 | 1 | 0.125 | 1 | 0.125 | 0.25 | SYN |

TABLE 4-continued

Interactions between diiodohydroxyquinoline and vancomycin against *C. difficile* clinical isolates.

| | MIC (μg/ml) | | | | | |
|---|---|---|---|---|---|---|
| | Vancomycin | | DIHQ | | | |
| *C. difficile* strains | Alone | Combined with DIHQ | Alone | Combined with vancomycin | [1]ΣFIC Index | Interpretation* |
| I6 | 0.5 | 0.06 | 2 | 0.5 | 0.375 | SYN |
| I9 | 1 | 0.125 | 0.06 | 0.06 | 1.125 | ADD |

Figure 4:
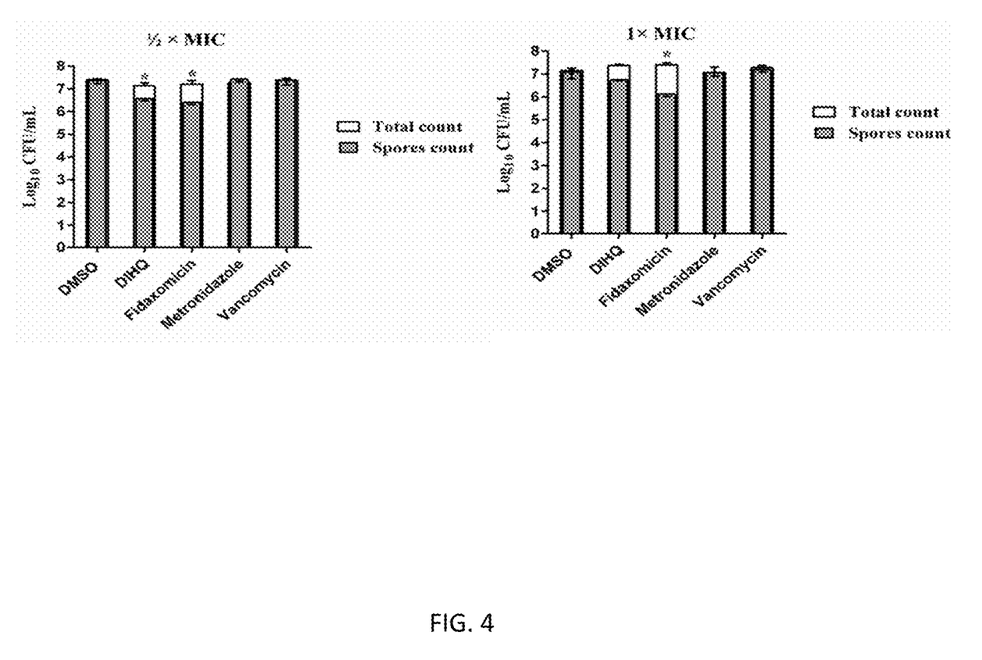
FIG. 4 shows spore inhibition of activity of diiodohydroxyquinoline (DIHQ) against *C. difficile* compared to the control anti-clostridial drugs; fidaxomicin, vancomycin and metronidazole against *C. difficile* NR-49277. Drugs at a concentration of 0.5×MIC and 1×MIC were incubated with bacteria for five days followed by serial dilution and plating to count both total bacterial count and spores count. DMSO (solvent of the drugs) served as a negative control. Error bars represent standard deviation values from triplicate samples for each treatment.
Figure 5:
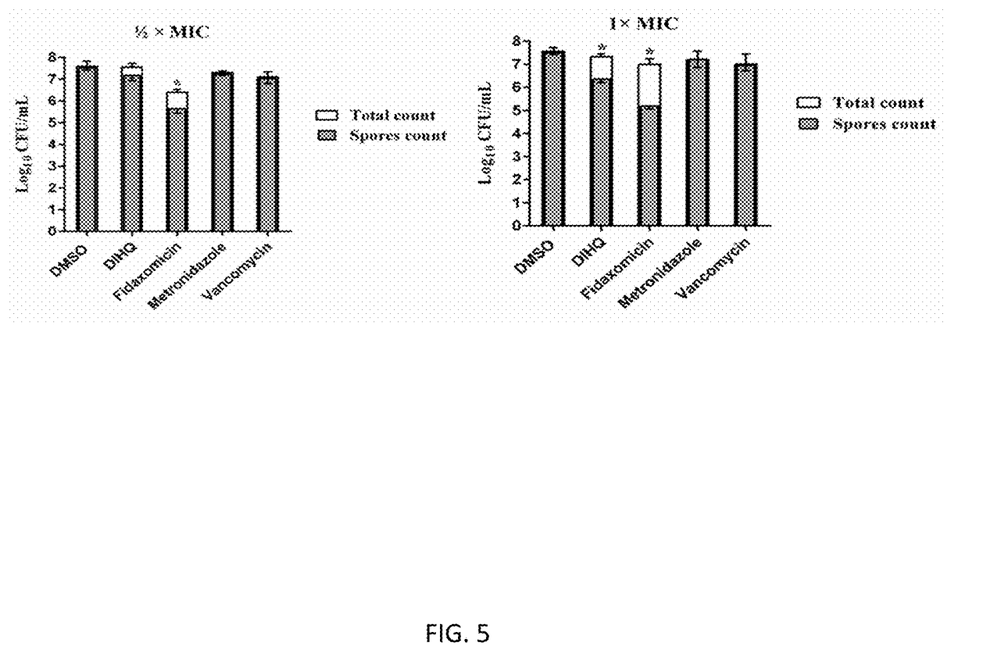
FIG. 5 shows spore inhibition of activity of diiodohydroxyquinoline (DIHQ) against *C. difficile* compared to the control anti-clostridial drugs; fidaxomicin, vancomycin and metronidazole against *C. difficile* ATCC 43255. Drugs at a concentration of 0.5×MIC and 1×MIC were incubated with bacteria for five days followed by serial dilution and plating to count both total bacterial count and spores count. DMSO (solvent of the drugs) served as a negative control. Error bars represent standard deviation values from triplicate samples for each treatment.

[1]ΣFIC; fractional inhibitory concentration
*ΣFIC index ≤0.5 is considered synergistic (SYN);
ΣFIC index >0.5 – 1.25 is considered additive (ADD);
ΣFIC index >1.25 – 4 is considered indifference (IND);
ΣFIC index >4 is considered antagonistic Additionally, toxin inhibition activity of DIHQ was investigated against 2 other hypervirulent *C. difficile* strains. When tested against *C. difficile* NR-49277, DIHQ displayed a significantly reduced spore count by nearly 0.56-$\log_{10}$ and 0.62-$\log_{10}$ at ½×MIC and 1×MIC, respectively (FIG. 4). Fidaxomicin significantly reduced *C. difficile* spore formation by nearly 0.8-$\log_{10}$ reduction (at ½×MIC) and 1.27-$\log_{10}$ reduction (at 1×MIC). On the other hand, almost no reduction in the spore count was observed with either vancomycin or metronidazole (FIG. 4). Moreover, when tested against *C. difficile* ATCC 43255, DIHQ reduced spore count by nearly 0.38-login and 0.99-login at ½×MIC and 1×MIC, respectively (FIG. 5). Fidaxomicin significantly reduced *C. difficile* spore formation by nearly 0.75-$\log_{10}$ reduction (at ½×MIC) and 1.8-$\log_{10}$ reduction (at 1×MIC). On the other hand, almost no reduction in the spore count was observed with either vancomycin or metronidazole (FIG. 5).

The Effect of Diiodohydroxyquinoline on *C. difficile* Toxin Production

Figure 6:
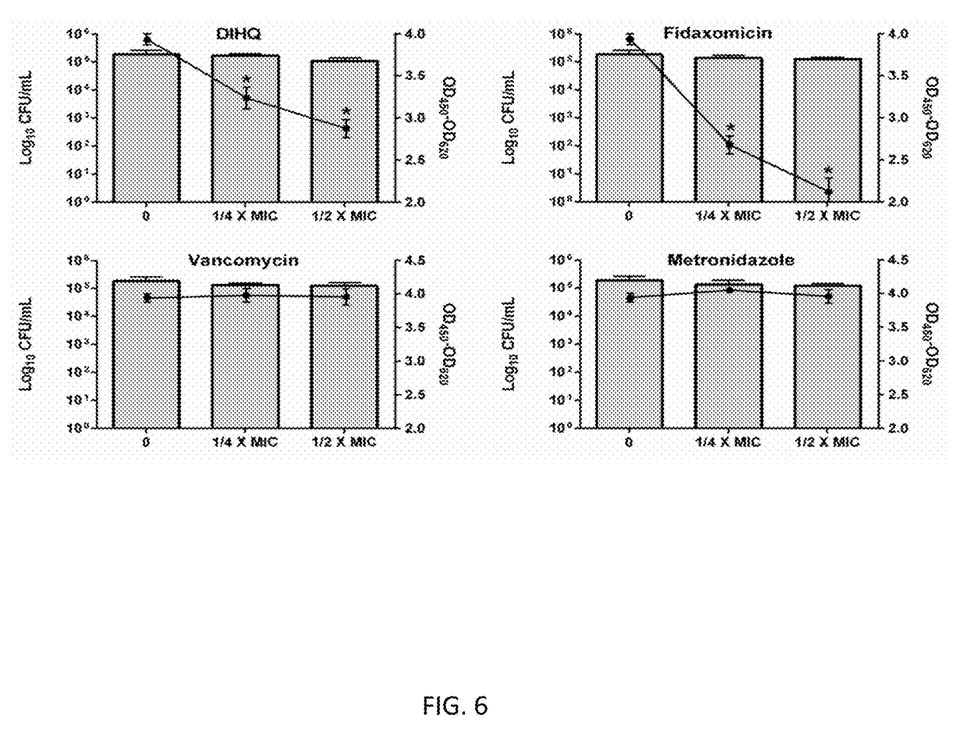
Figure 7:
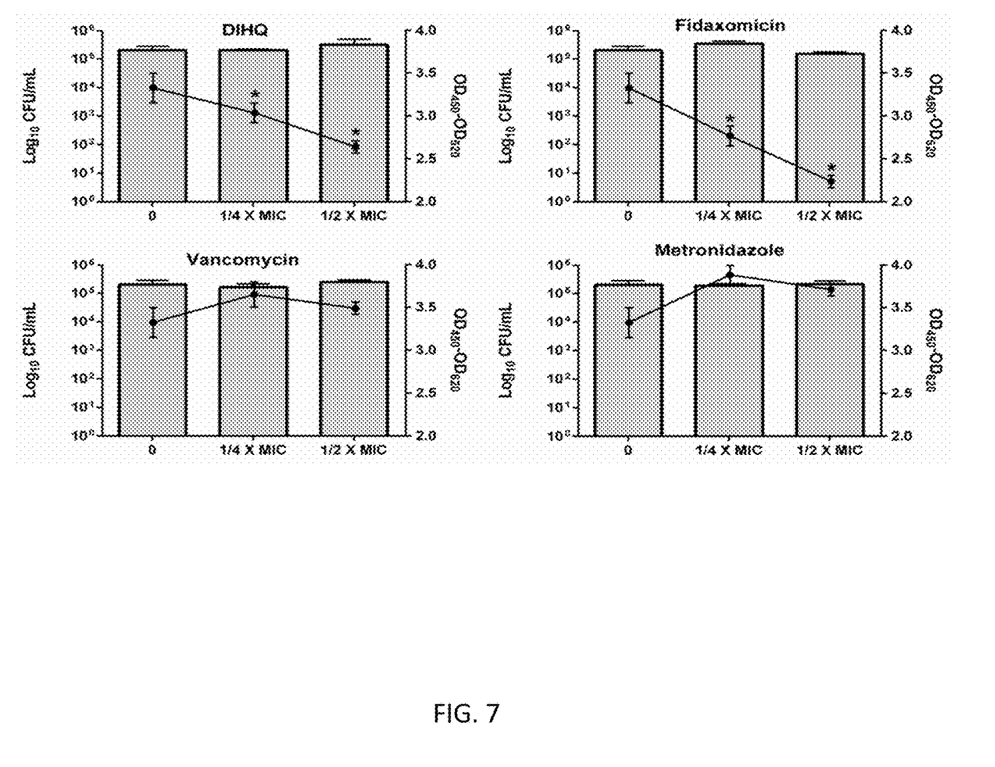
Figure 8:
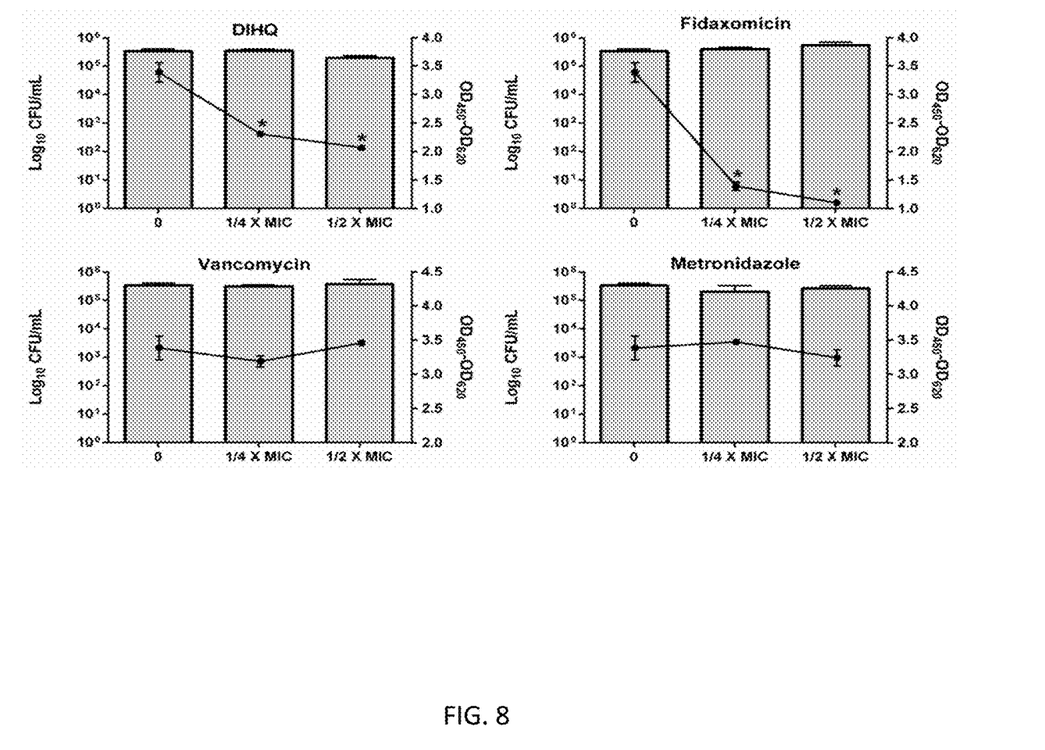

Toxins are the main virulence factor of *C. difficile*. Toxigenic *C. difficile* strains are capable of inducing inflammation and provoking pseudomembranous colitis. TcdA and TcdB can inactivate host GTPases, including Rac, Rho and CDC42 resulting in rearrangement of the actin cytoskeleton, intense inflammation, enormous fluid secretion, disruption of mucosal layer barrier function and finally necrosis and apoptosis of the colonic mucosal layer [50, 51]. Moreover, *C. difficile* increases toxin production during the stationary phase of growth where the majority of antibiotics are not as effective [46]. Therefore, agents capable of inhibiting *C. difficile* toxin production may contribute to effective treatment of CDI by limiting damage to the host's intestinal mucosa. Fidaxomicin is the only currently available anticlostridial drug with antitoxin activity [37]. We tested the *C. difficile* toxin inhibition activity of DIHQ, at subinhibitory concentrations, against hypervirulent toxigenic *C. difficile* strains. DIHQ (at ½×MIC) inhibited 17.8% and 27% of the total toxin production by *C. difficile* ATCC BAA-1870, at ¼×MIC and ½×MIC respectively (FIG. 6). Fidaxomicin, which is known to inhibit toxin production [37], inhibited 31.9% and 46.2% of toxin production at ¼×MIC and ½×MIC, respectively. No toxin inhibition was observed with either vancomycin or metronidazole (FIG. 6), in agreement with previous reports [52, 53]. Additionally, DIHQ's toxin inhibitory activity was tested against *C. difficile* ATCC 43255. DIHQ inhibited nearly 8% and 28.5% of total toxin production at ¼×MIC and ½×MIC respectively (FIG. 7). Fidaxomicin, which is known to inhibit toxin production, inhibited 14.3% and 37% of toxin production at ¼×MIC and ½×MIC, respectively. No toxin inhibition was observed with either vancomycin or metronidazole (FIG. 7). Moreover, toxin inhibitory activity was explored against a third hypervirulent *C. difficile* strain (*C. difficile* NR-49277). DIHQ inhibited nearly 31.8% and 38.9% of its total toxin production, at ¼×MIC and ½×MIC respectively (FIG. 8). Fidaxomicin inhibited 58.8% and 67.4% of toxin production at ¼×MIC and ½×MIC, respectively. No toxin inhibition was observed with either vancomycin or metronidazole (FIG. 8).

In Vitro Antimicrobial Evaluation of Diiodohydroxyquinoline Against Normal Microflora.

It is well known that the use of antibiotics/drugs which disturbs the normal and protective gut microflora allows gut pathogens like *C. difficile* to proliferate, colonize the gut and establish CDI [54]. Consequently, it is imperative to determine whether DIHQ has a deleterious effect on the normal gut microbiota or not. We tested the antibacterial activity of DIHQ and the control anticlostridial drugs against representative bacteria that comprise the human gut microbiome, including species of *Lactobacillus*, *Bacteroides* and *Bifidobacterium*. As presented in Table 5, DIHQ did not inhibit growth of species of *Bacteroides* and *Bifidobacterium*, up to the maximum tested concentration of 128 μg/mL (except *Bifidobacterium longum* (MIC=64-128 μg/mL), *B. adolescentis* and *B. angulatum* (MIC=128 μg/mL)). This was in contrast to metronidazole, which inhibited growth of all species of *Bacteroides* and *Bifidobacterium* tested, at concentrations that ranged from ≤1 μg/mL up to 2 μg/mL. Additionally, DIHQ exhibited weak antibacterial activity against both *Lactobacillus casei* (MIC=16 μg/mL) and *L. crispatus* (MIC=64 μg/mL) while it did not inhibit growth of *L. reuteri* (MIC>128 μg/mL). Fidaxomicin did not inhibit growth of *Lactobacillus* and *Bacteroides* strains tested (with the exception of *B. dorei* HM-719) up to a concentration of 128 μg/mL. Though, it exhibited a similar activity to metronidazole against *Bifidobacterium* strains. Similarly, vancomycin inhibited the growth of *Bifidobacterium* strains tested (MICs≤1 μg/mL) and *Lactobacillus* crispatus HM-371 (MIC=4 μg/mL).

TABLE 5

The antibacterial activity (MICs in μg/mL) of Diiodohydroxyquinoline and control drugs against representative human normal gut microbiota strains

| Bacterial Strains | DIHQ | Vancomycin | Metronidazole | Fidaxomicin |
|---|---|---|---|---|
| *Lactobacillus reuteri* HM-102 | >128 | >128 | >128 | >128 |
| *Lactobacillus casei* ATCC 334 | 16 | >128 | 16 | >128 |
| *Lactobacillus crispatus* HM-371 | 64 | 4 | >128 | >128 |
| *Bacteroides dorei* HM-719 | >128 | 64 | ≤1 | 128 |
| *Bacteroides dorei* HM-717 | >128 | 128 | ≤1 | >128 |
| *Bacteroides dorei* HM-718 | >128 | 128 | ≤1 | >128 |
| *Bacteroides dorei* HM-29 | >128 | 64 | ≤1 | >128 |
| *Bacteroides fragilis* HM-711 | >128 | 128 | ≤1 | >128 |
| *Bacteroides fragilis* HM-709 | >128 | 64 | 2 | >128 |
| *Bacteroides fragilis* HM-710 | >128 | 64 | 2 | >128 |
| *Bacteroides fragilis* HM-714 | >128 | 128 | ≤1 | >128 |
| *Bifidobacterium adolescentis* HM-633 | 128 | ≤1 | ≤1 | ≤1 |
| *Bifidobacterium angulatum* HM-1189 | 128 | ≤1 | ≤1 | ≤1 |
| *Bifidobacterium breve* HM-411 | >128 | ≤1 | 2 | 2 |
| *Bifidobacterium breve* HM-1120 | >128 | ≤1 | ≤1 | ≤1 |
| *Bifidobacterium longum* HM-845 | 64 | ≤1 | ≤1 | ≤1 |
| *Bifidobacterium longum* HM-847 | 128 | ≤1 | ≤1 | ≤1 |

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES

1. Vindigni, S. M. and C. M. Surawicz, *C. difficile Infection: Changing Epidemiology and Management Paradigms*. Clin Trans Gastroenterol, 2015. 6: p. e99.
2. Lessa, F. C., et al., *Burden of Clostridium difficile infection in the United States*. N Engl J Med, 2015. 372(9): p. 825-34.
3. Depestel, D. D. and D. M. Aronoff, *Epidemiology of Clostridium difficile infection*. J Pharm Pract, 2013. 26(5): p. 464-75.
4. Gupta, A. and S. Khanna, *Community-acquired Clostridium difficile infection: an increasing public health threat*. Infection and Drug Resistance, 2014. 7: p. 63-72.
5. Bauer, M. P., et al., *Community-onset Clostridium difficile-associated diarrhoea not associated with antibiotic usage*. Netherlands Journal of Medicine, 2008. 66(5): p. 207-211.
6. McDonald, L. C., et al., *Clinical Practice Guidelines for Clostridium difficile Infection in Adults and Children: 2017 Update by the Infectious Diseases Society of America (IDSA) and Society for Healthcare Epidemiology of America (SHEA)*. Clin Infect Dis, 2018.66(7): p. 987-994.
7. Vardakas, K. Z., et al., *Treatment failure and recurrence of Clostridium difficile infection following treatment with vancomycin or metronidazole: a systematic review of the evidence*. Int J Antimicrob Agents, 2012. 40(1): p. 1-8.
8. Baines, S. D. and M. H. Wilcox, *Antimicrobial Resistance and Reduced Susceptibility in Clostridium difficile: Potential Consequences for Induction, Treatment, and Recurrence of C. difficile Infection*. Antibiotics (Basel), 2015. 4(3): p. 267-98.
9. Cornely, O. A., et al., *Treatment of first recurrence of Clostridium difficile infection: fidaxomicin versus vancomycin*. Clin Infect Dis, 2012. 55 Suppl 2: p. S154-61.
10. Orenstein, R., *Fidaxomicin failures in recurrent Clostridium difficile infection: a problem of timing*. Clin Infect Dis, 2012. 55(4): p. 613-4.
11. DiMasi, J. A., R. W. Hansen, and H. G. Grabowski, *The price of innovation: new estimates of drug development costs*. J Health Econ, 2003. 22(2): p. 151-85.
12. Thangamani, S., et al., *Antibacterial activity and mechanism of action of auranofin against multi-drug resistant bacterial pathogens*. Sci Rep, 2016. 6: p. 22571.
13. Thangamani, S., et al., *Repurposing Approach Identifies Auranofin with Broad Spectrum Antifungal Activity That Targets Mia40-Erv1 Pathway*. Frontiers in Cellular and Infection Microbiology, 2017. 7.
14. Thangamani, S., et al., *Ebselen exerts antifungal activity by regulating glutathione (GSH) and reactive oxygen species (ROS) production in fungal cells*. Biochim Biophys Acta Gen Subj, 2017. 1861(1 Pt A): p. 3002-3010.
15. Abutaleb, N. S. and M. N. Seleem, *Auranofin, at clinically achievable dose, protects mice and prevents recurrence from Clostridioides difficile infection*. Scientific Reports, 2020. 10(1): p. 1-8.
16. Mohammad, H., N. S. Abutaleb, and M. N. Seleem, *Auranofin Rapidly Eradicates Methicillin-resistant Staphylococcus aureus (MRSA) in an Infected Pressure Ulcer Mouse Model*. Sci Rep, 2020. 10(1): p. 7251.
17. Abutaleb, N. S. and M. N. Seleem, *Antivirulence activity of auranofin against vancomycin-resistant enterococci: in vitro and in vivo studies*. Int J Antimicrob Agents, 2020. 55(3): p. 105828.
18. AbdelKhalek, A., et al., *Antibacterial and antivirulence activities of auranofin against Clostridium difficile*. Int J Antimicrob Agents, 2019. 53(1): p. 54-62.
19. Eldesouky, H. E., et al., *Synergistic interactions of sulfamethoxazole and azole antifungal drugs against emerging multidrug-resistant Candida auris*. Int J Antimicrob Agents, 2018. 52(6): p. 754-761.
20. AbdelKhalek, A., et al., *Repurposing ebselen for decolonization of vancomycin-resistant enterococci (VRE)*. PLoS One, 2018. 13(6): p. e0199710.
21. Mohammad, H., et al., *Repurposing niclosamide for intestinal decolonization of vancomycin-resistant enterococci*. Int J Antimicrob Agents, 2018. 51(6): p. 897-904.
22. AbdelKhalek, A., et al., *Repurposing auranofin as an intestinal decolonizing agent for vancomycin-resistant enterococci*. Scientific reports, 2018. 8(1): p. 1-9.
23. Kappagoda, S., U. Singh, and B. G. Blackburn, *Antiparasitic therapy*. Mayo Clin Proc, 2011. 86(6): p. 561-83.
24. Ghaskadbi, S. and V. G. Vaidya, *In vivo antimutagenic effect of ascorbic acid against mutagenicity of the common antiamebic drug diiodohydroxyquinoline*. Mutat Res, 1989. 222(3): p. 219-22.
25. Mody, D., A. I. M. Athamneh, and M. N. Seleem, *Curcumin: A natural derivative with antibacterial activity against Clostridium difficile*. J Glob Antimicrob Resist, 2019.
26. Shao, X., et al., *Chemical Space Exploration Around Thieno[3,2-d]pyrimidin-4(3H)-one Scaffold led to a Novel Class of Highly Active Clostridium difficile Inhibitors*. J Med Chem, 2019.
27. Abutaleb, N. S. and M. N. Seleem, *Repurposing the Antiamoebic Drug Diiodohydroxyquinoline for Treatment of Clostridioides difficile Infections*. Antimicrob Agents Chemother, 2020. 64(6).
28. AbdelKhalek, A., et al., *Screening for potent and selective anticlostridial leads among FDA-approved drugs*. The Journal of Antibiotics, 2020. 73(6): p. 392-409.
29. Pal, R. and M. N. Seleem, *Screening of Natural Products and Approved Oncology Drug Libraries for Activity against Clostridioides difficile*. Sci Rep, 2020. 10(1): p. 5966.
30. Hammad, A., et al., *From Phenylthiazoles to Phenylpyrazoles: Broadening the Antibacterial Spectrum toward Carbapenem-Resistant Bacteria*. J Med Chem, 2019. 62(17): p. 7998-8010.
31. Elsebaei, M. M., et al., *Lipophilic efficient phenylthiazoles with potent undecaprenyl pyrophosphatase inhibitory activity*. Eur J Med Chem, 2019. 175: p. 49-62.

32. Kumar, M., S. Adhikari, and J. G. Hurdle, *Action of nitroheterocyclic drugs against Clostridium difficile*. International Journal of Antimicrobial Agents, 2014. 44(4): p. 314-319.
33. Martinezlrujo, J. J., et al., *A checkerboard method to evaluate interactions between drugs*. Biochemical Pharmacology, 1996. 51(5): p. 635-644.
34. Mohammad, H., M. Cushman, and M. N. Seleem, *Antibacterial Evaluation of Synthetic Thiazole Compounds In Vitro and In Vivo in a Methicillin-Resistant Staphylococcus aureus (MRSA) Skin Infection Mouse Model*. Plos One, 2015. 10(11).
35. Meletiadis, J., et al., *Defining Fractional Inhibitory Concentration Index Cutoffs for Additive Interactions Based on Self-Drug Additive Combinations, Monte Carlo Simulation Analysis, and In Vitro-In Vivo Correlation Data for Antifungal Drug Combinations against Aspergillus fumigatus*. Antimicrob Agents Chemother, 2010. 54(2): p. 602-609.
36. Garneau, J. R., L. Valiquette, and L. C. Fortier, *Prevention of Clostridium difficile spore formation by sub-inhibitory concentrations of tigecycline and piperacillin/tazobactam*. Bmc Infectious Diseases, 2014. 14.
37. Babakhani, F., et al., *Fidaxomicin inhibits toxin production in Clostridium difficile*. Journal of Antimicrobial Chemotherapy, 2013. 68(3): p. 515-522.
38. Kushiro, A., et al., *Antimicrobial susceptibility testing of lactic acid bacteria and bifidobacteria by broth microdilution method and Etest*. Int J Food Microbiol, 2009. 132(1): p. 54-8.
39. C.a.L.S. Institute, M.f.D.A.S.t.f.b.t.G.A.A.S.-t.e., 2012, M07-A9.
40. Lofmark, S., C. Edlund, and C. E. Nord, *Metronidazole Is Still the Drug of Choice for Treatment of Anaerobic Infections*. Clinical Infectious Diseases, 2010. 50: p. S16-S23.
41. Rybak, M. J. and B. J. McGrath, *Combination antimicrobial therapy for bacterial infections—Guidelines for the clinician*. Drugs, 1996. 52(3): p. 390-405.
42. Sanders, C. V. and K. E. Aldridge, *Antimicrobial Therapy of Anaerobic Infections*, 1991. Pharmacotherapy, 1991. 11(2): p. S72-S79.
43. Buggy, B. P., R. Fekety, and J. Silva, *Therapy of Relapsing Clostridium-Difficile Associated Diarrhea and Colitis with the Combination of Vancomycin and Rifampin*. Journal of Clinical Gastroenterology, 1987. 9(2): p. 155-159.
44. Erikstrup, L. T., et al., *Treatment of Clostridium difficile infection in mice with vancomycin alone is as effective as treatment with vancomycin and metronidazole in combination*. Bmj Open Gastroenterology, 2015. 2(1).
45. Asrani, C. H., et al., *Efficacy and Safety of Metronidazole Versus a Combination of Metronidazole and Diiodohydroxyquinoline for the Treatment of Patients with Intestinal Amebiasis—a Primary-Care Physicians Research Group-Study* (Vol 56, Pg 678, 1995). Current Therapeutic Research-Clinical and Experimental, 1995. 56(10): p. 1111-1111.
46. Vedantam, G., et al., *Clostridium difficile infection: toxins and non-toxin virulence factors, and their contributions to disease establishment and host response*. Gut Microbes, 2012. 3(2): p. 121-34.
47. Gerding, D. N., C. A. Muto, and R. C. Owens, *Measures to control and prevent Clostridium difficile infection*. Clinical Infectious Diseases, 2008. 46: p. S43-S49.
48. Kamboj, M., et al., *Relapse versus reinfection: surveillance of Clostridium difficile infection*. Clin Infect Dis, 2011. 53(10): p. 1003-6.
49. Babakhani, F., et al., *Fidaxomicin Inhibits Spore Production in Clostridium difficile*. Clinical Infectious Diseases, 2012. 55: p. S162-5169.
50. Davies, A. H., et al., *Super toxins from a super bug: structure and function of Clostridium difficile toxins*. Biochem J, 2011. 436(3): p. 517-26.
51. Chumbler, N. M., et al., *Clostridium difficile Toxin B Causes Epithelial Cell Necrosis through an Autoprocessing-Independent Mechanism*. Plos Pathogens, 2012. 8(12).
52. Endres, B. T., et al., *Evaluating the Effects of Surotomycin Treatment on Clostridium difficile Toxin A and B Production, Immune Response*, and *Morphological Changes*. Antimicrob Agents Chemother, 2016. 60(6): p. 3519-23.
53. Locher, H. H., et al., *In vitro and in vivo antibacterial evaluation of cadazolid, a new antibiotic for treatment of Clostridium difficile infections*. Antimicrob Agents Chemother, 2014. 58(2): p. 892-900.
54. Kim, S., A. Covington, and E. G. Pamer, *The intestinal microbiota: Antibiotics, colonization resistance, and enteric pathogens*. Immunological Reviews, 2017. 279 (1): p. 90-105.

We claim:

1. A method of treating a patient previously infected by *Clostridium difficile* comprising administering a therapeutically effective spore-inhibiting amount of 5,7-diiodoquinolin-8-ol, together with one or more agents, wherein the agent is vancomycin or fidaxomicin, and one or more pharmaceutically acceptable carriers, diluents, and excipients, to the patient in need of relief from recurrence of said infection.

2. The method of claim 1, the method comprises administering said 5,7-diiodoquinolin-8-ol orally.

3. The method of claim 1, wherein the method comprises administering said 5,7-diiodoquinolin-8-ol topically.

4. The method of claim 1, the method comprises administering combination of said 5,7-diiodoquinolin-8-ol and one or more agents at the same time.

5. The method of claim 1, the method comprises administering said 5,7-diiodoquinolin-8-ol and one or more agents separately.

6. The method of claim 1, the method comprises administering said 5,7-diiodoquinolin-8-ol and one or more agents sequentially.

* * * * *